US00PP20791P2

(12) United States Plant Patent
Jacobs

(10) Patent No.: US PP20,791 P2
(45) Date of Patent: Feb. 23, 2010

(54) ***ALSTROEMERIA* PLANT NAMED 'ZALSACAL'**

(50) Latin Name: *Alstroemeria hybrida*
Varietal Denomination: Zalsacal

(75) Inventor: Henricus Cornelius Maria Jacobs, Rijsenhout (NL)

(73) Assignee: Van Zanten Plants b.v., Hillegom (NL)

( * ) Notice: Subject to any disclaimer, the term of this patent is extended or adjusted under 35 U.S.C. 154(b) by 0 days.

(21) Appl. No.: 12/291,394

(22) Filed: Nov. 7, 2008

(51) Int. Cl.
*A01H 5/00* (2006.01)

(52) U.S. Cl. ..... Plt./309

(58) Field of Classification Search ..... Plt./309
See application file for complete search history.

*Primary Examiner*—Susan B McCormick Ewoldt
(74) *Attorney, Agent, or Firm*—C. A. Whealy

(57) ABSTRACT

A new and distinct cultivar of *Alstroemeria* plant named 'Zalsacal', characterized by its erect and strong flowering stems; vigorous growth habit; pink and red-colored flowers; and excellent postproduction longevity.

1 Drawing Sheet

Botanical designation: *Alstroemeria hybrida.*
Cultivar denomination: 'Zalsacal'.

BACKGROUND OF THE INVENTION

The present invention relates to a new and distinct cultivar of *Alstroemeria* plant, botanically known as *Alstroemeria hybrida*, commercially used as a cut flower *Alstroemeria*, and hereinafter referred to by the name 'Zalsacal'.

The new *Alstroemeria* plant is a product of a planned breeding program conducted by the Inventor in Rijsenhout, The Netherlands. The objective of the breeding program is to create new cut flower *Alstroemeria* cultivars with desirable flower and plant qualities, attractive foliage and flower coloration and excellent postproduction longevity.

The new *Alstroemeria* plant originated from a cross-pollination made by the Inventor in Rijsenhout, The Netherlands in May, 2003, of a proprietary *Alstroemeria hybrida* selection identified as code number 00- 0621-05, not patented, as the female, or seed, parent with a proprietary *Alstroemeria hybrida* selection identified as code number 90-0141-02, not patented, as the male, or pollen, parent. The new *Alstroemeria* was discovered and selected by the Inventor as a flowering plant from within the progeny of the stated cross-pollination in a controlled greenhouse environment in Rijsenhout, The Netherlands in June, 2004.

Asexual reproduction of the new *Alstroemeria* plant by rhizome divisions in a controlled greenhouse environment in Rijsenhout, The Netherlands since September, 2004, has shown that the unique features of this new *Alstroemeria* plant are stable and reproduced true to type in successive generations.

SUMMARY OF THE INVENTION

Plants of the new *Alstroemeria* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Zalsacal'.

These characteristics in combination distinguish 'Zalsacal' as a new and distinct cultivar of *Alstroemeria* plant:

1. Erect and strong flowering stems.
2. Vigorous growth habit.
3. Pink and red-colored flowers.
4. Excellent postproduction longevity.

Plants of the new *Alstroemeria* can be compared to plants of the female parent selection. Plants of the new *Alstroemeria* differ from plants of the female parent selection in the following characteristics:

1. Plants of the new *Alstroemeria* have larger flowers than plants of the female parent selection.
2. Plants of the new *Alstroemeria* and the female parent selection differ in flower color as plants of the female parent selection have red-colored flowers.

Plants of the new *Alstroemeria* can be compared to plants of the male parent selection. Plants of the new *Alstroemeria* differ from plants of the male parent selection primarily in flower color as plants of the male parent selection have yellow-colored flowers.

Plants of the new *Alstroemeria* can be compared to plants of *Alstroemeria hybrida* 'Stabec', disclosed in U.S. Plant Pat. No. 9,041. In side-by-side comparisons conducted in Rijsenhout, The Netherlands, plants of the new *Alstroemeria* differed primarily from plants of 'Stabec' in flower color as plants of 'Stabec' had flowers that were white and light red to deep pink in color. In addition, plants of the new *Alstroemeria* were slightly shorter and had slightly smaller flowers than plants of 'Stabec'.

BRIEF DESCRIPTION OF THE PHOTOGRAPH

The accompanying colored photograph illustrates the overall appearance of the new *Alstroemeria*, showing the colors as true as it is reasonably possible to obtain in colored reproductions of this type. Colors in the photograph may differ slightly from the color values cited in the detailed botanical description which accurately describe the colors of the new *Alstro-*

*emeria*. The photograph comprises a side perspective view of a typical flowering stem of 'Zalsacal'.

DETAILED BOTANICAL DESCRIPTION

The aforementioned photograph and following observations and measurements describe plants of the new *Alstroemeria* grown in Rijsenhout, The Netherlands in a glass-covered greenhouse in ground beds. During the production of the plants, day temperatures ranged from 15° C. to 20° C., night temperatures ranged from 10° C. to 15° C. and light levels averaged 5,000 lux. Plants used for the photograph and description had been growing for one year. The photograph and the description were taken in the late sununer. Color references are made to The Royal Horticultural Society Colour Chart, 1995 Edition, except where general terms of ordinary dictionary significance are used.

Botanical classification: *Alstroemeria hybrida* 'Zalsacal'.

Parentage:

*Female, or seed, parent.*—Proprietary *Alstroemeria hybrida* selection identified as code number 00-0621-05, not patented.

*Male or pollen parent.*—Proprietary *Alstroemeria hybrida* selection identified as code number 90-0141-02, not patented.

Propagation:

*Type.*—By tissue culture.

*Time to produce a rooted young plant, summer.*—About 40 days.

*Time to produce a rooted young plant, winter.*—About 60 days.

*Root description.*—Fibrous, fleshy, thick; close to 155D in color.

*Rooting habit.*—Freely branching; moderately dense.

*Rhizomes.*—Shape: Elongate; rounded. Length: About 10 cm to 30 cm. Diameter: About 3 mm to 10 mm. Texture: Smooth. Color: Close to 155D.

Plant description:

*Plant and growth habit.*—Upright; freely branching, bushy appearance; vigorous growth habit.

*Time from planting to harvest of cut flowers.*—About 80 to 90 days.

*Number of flowering stems produced per year.*—About 240 to 280.

*Plant height.*—About 100 cm to 140 cm.

*Plant diameter (spread).*—About 35 cm.

Flowering stem description:

*Aspect.*—Erect.

*Length.*—About 120 cm.

*Diameter.*—About 8 mm to 10 mm.

*Internode length.*—About 5 cm to 6 cm.

*Strength.*—Strong.

*Texture.*—Smooth, glabrous.

*Color.*—Close to 146C; towards the base, overlain with close to 183A.

Foliage description:

*Appearance.*—Leaves asymmetrical; sessile.

*Length.*—About 18 cm to 25 cm.

*Width.*—About 2.8 cm to 4.3 cm.

*Shape.*—Lanceolate.

*Apex.*—Acute.

*Base.*—Attenuate.

*Margin.*—Entire; slightly undulate.

*Texture, upper and lower surfaces.*—Smooth, glabrous.

*Venation pattern.*—Parallel.

*Color.*—Developing and fully developed leaves, upper surface: Close to 147A; venation, close to 147A. Developing and fully developed leaves, lower surface: Close to 147B; venation, close to 147B.

Flower description:

*Flower type and habit.*—Single cup-shaped flowers arranged in compound umbels. Flowers face mostly outwardly. Perianth segments separate. Freely and continuously flowering.

*Natural flowering season.*—Flowering continuous during the spring in The Netherlands.

*Fragrance.*—Not detected.

*Flower longevity on the plant.*—About four weeks; flowers not persistent.

*Flower longevity as a cut flower.*—About 12 to 16 days.

*Flower buds (showing color).*—Length: About 4.5 cm to 5 cm. Diameter: About 1.5 cm to 1.8 cm. Shape: Roughly ovoid. Color: Close to 53A.

*Umbel height.*—About 12 cm to 18 cm.

*Umbel diameter.*—About 16 cm to 18.5 cm.

*Number of flowers per umbel.*—About 9 to 32.

*Flower diameter.*—About 6 cm to 7 cm.

*Flower length (height).*—About 7.5 cm to 8.5 cm.

*Flower depth.*—About 6.5 cm to 7.5 cm.

*Perianth.*—Arrangement: Six arranged in two whorls, each whorl with two lateral and one median segments. Outer perianth, lateral segments: Length: About 5.5 cm to 6 cm. Width: About 3 cm to 3.2 cm. Shape: Obovate. Apex: Embedded pointed. Base: Attenuate. Margin: Entire; weakly undulate. Texture, upper and lower surfaces: Smooth, glabrous. Color, when opening and fully opened, upper surface: Close to 48A; blotch, close to 52A; towards the apex, greenish overtones; occasional stripes, close to 183A. Color, when opening and fully opened, lower surface: Close to 48A; blotch, close to 52A; towards the apex and venation, greenish overtones. Outer perianth, median segment: Length: About 5.4 cm to 6.2 cm. Width: About 2.9 cm to 3.4 cm. Shape: Obovate. Apex: Embedded pointed. Base: Attenuate. Margin: Entire; weakly undulate. Texture, upper and lower surfaces: Smooth, glabrous. Color, when opening and fully opened, upper surface: Close to 48A; blotch, close to 52A; towards the apex, greenish overtones; occasional stripes, close to 183A. Color, when opening and fully opened, lower surface: Close to 48A; blotch, close to 52A; towards the apex and venation, greenish overtones. Inner perianth, lateral segments: Length: About 6 cm to 6.9 cm. Width: About 1.6 cm to 1.8 cm. Shape: Oblanceolate. Apex: Wishbone-shaped. Base: Attenuate. Margin: Entire; weakly undulate. Texture, upper and lower surfaces: Smooth, glabrous. Color, when opening and fully opened, upper surface: Close to 48A; blotch, close to 52A; center and towards the base, close to 8A; stripes, close to 183A. Color, when opening and fully opened, lower surface: Close to 48A; blotch, close to 52A; center and towards the base, close to 8A; stripes, close to 183A. Inner perianth, median segment: Length: About 5.6 cm to 5.9 cm. Width: About 1.5 cm to 1.7 cm. Shape: Oblanceolate. Apex: Wishbone-shaped. Base: Attenuate. Margin: Entire; weakly undulate. Texture, upper and lower surfaces: Smooth, glabrous. Color, when opening and fully opened, upper surface: Close to 48A; blotch, close to 52A; center and towards the base, close to 8A; stripes, close to 183A. Color, when opening and fully opened, lower surface: Close to 48A; blotch, close to 52A; center and towards the base, close to 8A; stripes, close to 183A.

*Peduncles.*—Length: About 4 cm to 10 cm. Diameter: About 2 mm to 4 mm. Strength: Strong. Angle: Erect to about 30° C. from vertical. Texture: Smooth, glabrous. Color: Close to 146B.

*Reproductive organs.*—Stamens: Quantity per flower: Six. Anther shape: Elliptical. Anther length: About 9 mm. Anther diameter: About 3 mm. Anther color: Close to 175A. Pollen amount: Scarce. Pollen color: Close to 163A. Pistils: Quantity per flower: One. Style length: About 2.5 cm to 3.5 cm. Style color: Close to 46A. Stigma color: Close to 46A. Ovary color: Close to 147B.

*Fruit/seed.*—Fruit and seed development has not been observed.

Disease/pest resistance: Plants of the new *Alstroemeria* have not been observed to be resistant to pathogens and pests common to *Alstroemeria*.

Temperature tolerance: Plants of the new *Alstroemeria* have been observed to tolerate temperatures from about −5° C. to about 40° C.

It is claimed:

1. A new and distinct *Alstroemeria* plant named 'Zalsacal' as illustrated and described.

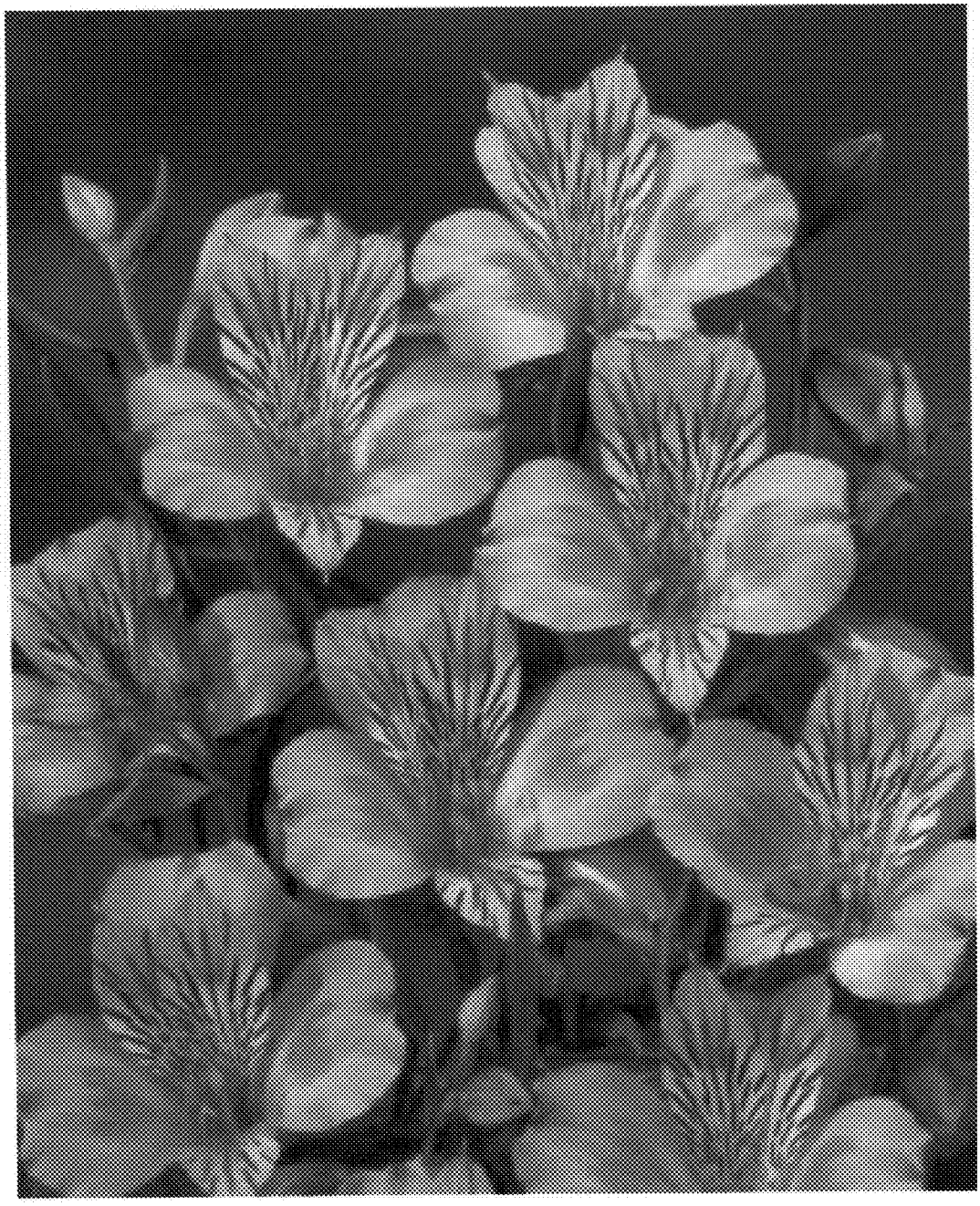

* * * * *